United States Patent
Yin et al.

(10) Patent No.: US 8,031,829 B2
(45) Date of Patent: Oct. 4, 2011

(54) METHOD FOR ANALYTIC RECONSTRUCTION OF CONE-BEAM PROJECTION DATA FOR MULTI-SOURCE INVERSE GEOMETRY CT SYSTEMS

(75) Inventors: Zhye Yin, Schenectady, NY (US); Bruno Kristiaan Bernard DeMan, Clifton Park, NY (US); Jed Douglas Pack, Glenville, NY (US)

(73) Assignee: General Electric Company, Niskayuna, NY (US)

( * ) Notice: Subject to any disclaimer, the term of this patent is extended or adjusted under 35 U.S.C. 154(b) by 675 days.

(21) Appl. No.: 11/924,829

(22) Filed: Oct. 26, 2007

(65) Prior Publication Data

US 2009/0110259 A1    Apr. 30, 2009

(51) Int. Cl.
*A61B 6/03* (2006.01)
(52) U.S. Cl. .................................. 378/9; 378/4
(58) Field of Classification Search ........... 378/4–20; 382/128–131
See application file for complete search history.

(56) References Cited

U.S. PATENT DOCUMENTS

| | | | | |
|---|---|---|---|---|
| 5,825,842 | A * | 10/1998 | Taguchi | 378/15 |
| 6,597,756 | B1 * | 7/2003 | Basu et al. | 378/15 |
| 6,754,299 | B2 * | 6/2004 | Patch | 378/15 |
| 2002/0141531 | A1 * | 10/2002 | Taguchi | 378/19 |
| 2003/0007593 | A1 * | 1/2003 | Heuscher et al. | 378/4 |
| 2005/0190878 | A1 * | 9/2005 | De Man et al. | 378/9 |

OTHER PUBLICATIONS

De Man et al., Multiple-source inverse geometry CT: a new system concept for X-ray computed tomography, Conference date Feb. 18, 2007, online publication date Mar. 13, 2007, SPIE, vol. 6510, pp. 65100H-1-65100H-8.*

Deque et al., Iterative Reconstruction for Multi-Source Inverse Geometry CT: a Feasibility Study, Conference date Feb. 18, 2007, online publication date Mar. 13, 2007, SPIE, vol. 6510, pp. 65105Y-1-65105Y-11.*

Tang et al., Helical and axial Cone Beam Filtered Backprojection (CB-FBP) Reconstruction Algorithms Using a General Window Function, 2005, 2005 IEEE Nuclear Science Conference Record, M03-352, pp. 1863-1866.*

Hsieh et al., Cone-angle dependent generalized weighting scheme for 16-slice helical CT, 2002, SPIE, vol. 4684, pp. 74-81.*

* cited by examiner

*Primary Examiner* — Edward Glick
*Assistant Examiner* — John Corbett
(74) *Attorney, Agent, or Firm* — Fletcher Yoder

(57) ABSTRACT

A method for analytically reconstructing a multi-axial computed tomography (CT) dataset, acquired using one or more longitudinally-offset x-ray beams emitted from multiple x-ray sources is provided. The method comprises acquiring one or more CT axial projection datasets, wherein the CT axial projection datasets are acquired using less than a full scan of data. The method further comprises reconstructing the CT axial projection datasets to generate a reconstructed image volume. The reconstruction comprises back projecting one or more voxels comprising the multi-axial CT dataset, along one or more projection views, based upon a cone-angle weight determined for the voxels, wherein the cone-angle weight for the voxels is determined along a longitudinal direction.

22 Claims, 12 Drawing Sheets

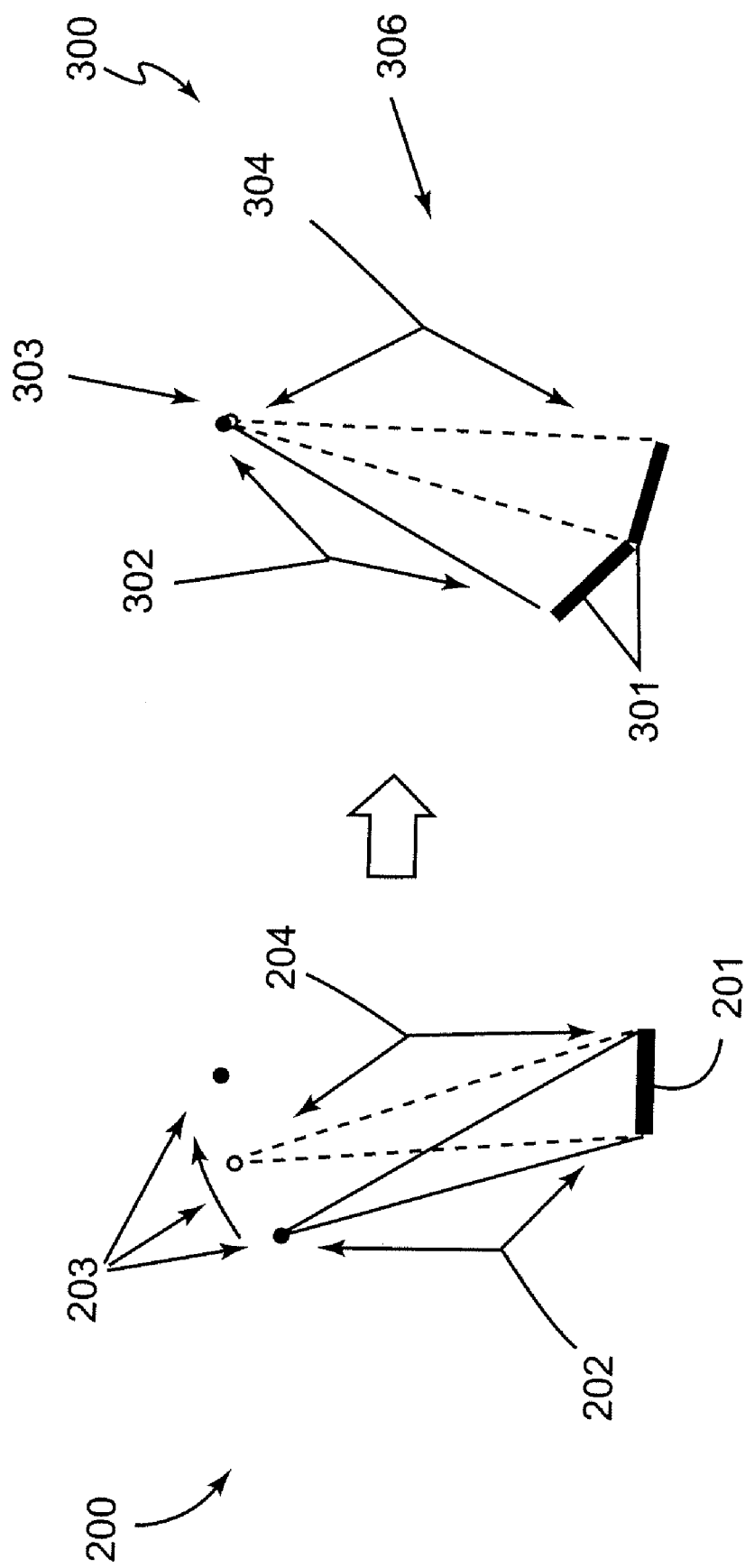

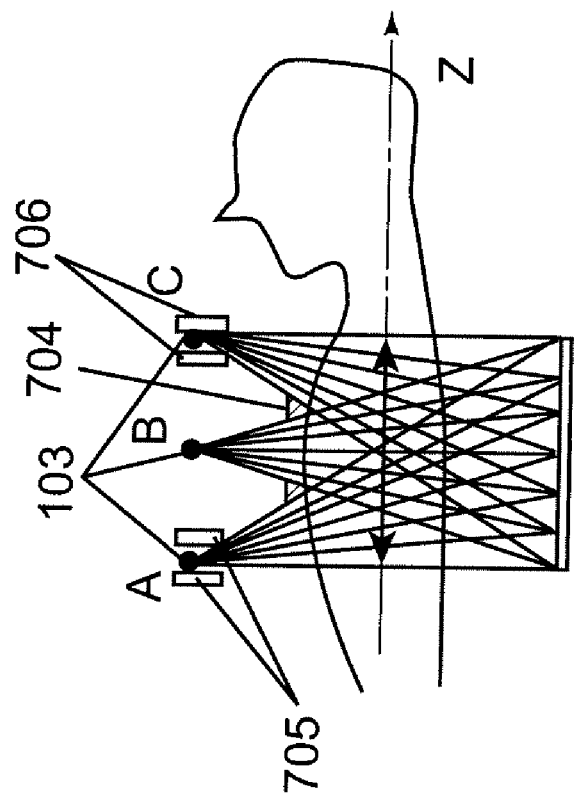
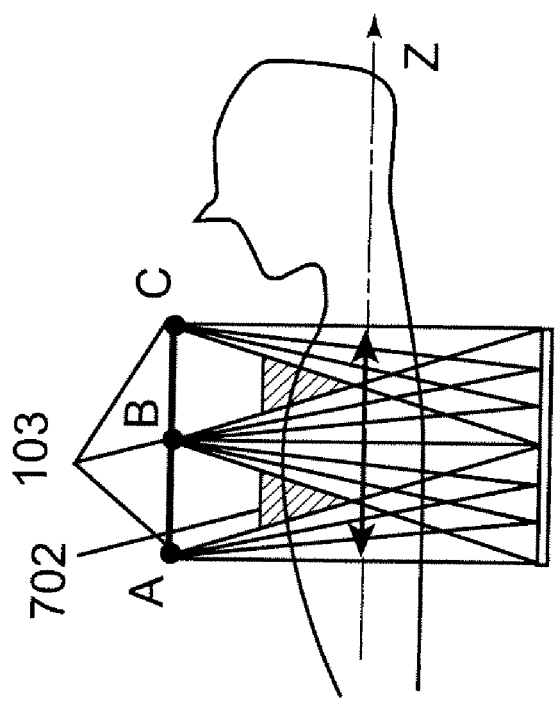
Fig. 7(b)
Fig. 7(a)

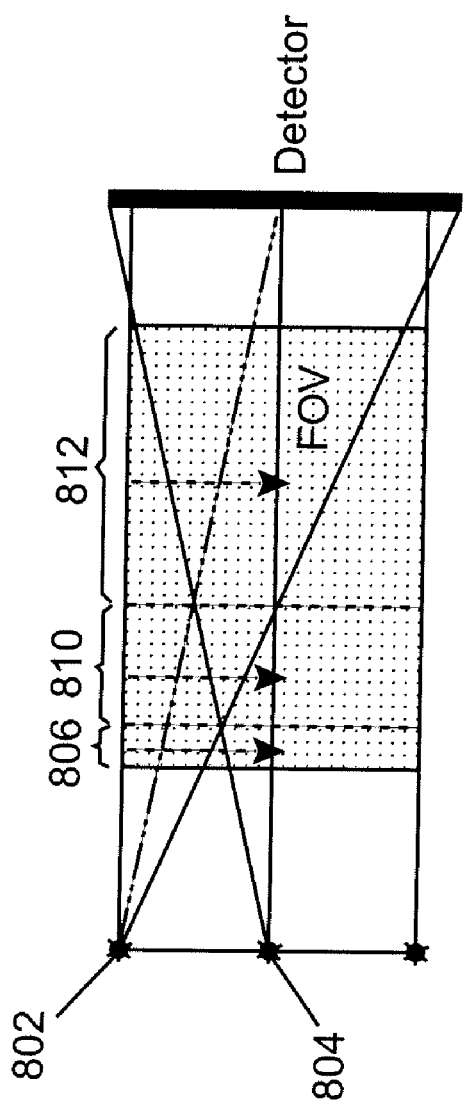
Fig. 8
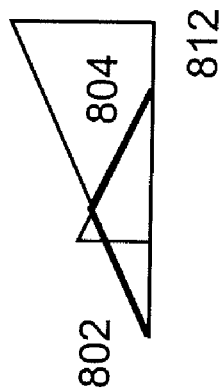
Fig. 8(a)
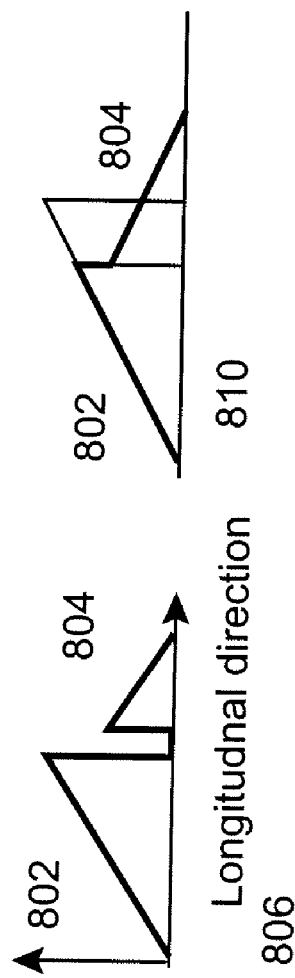
Fig. 8(b)
Fig. 8(c)

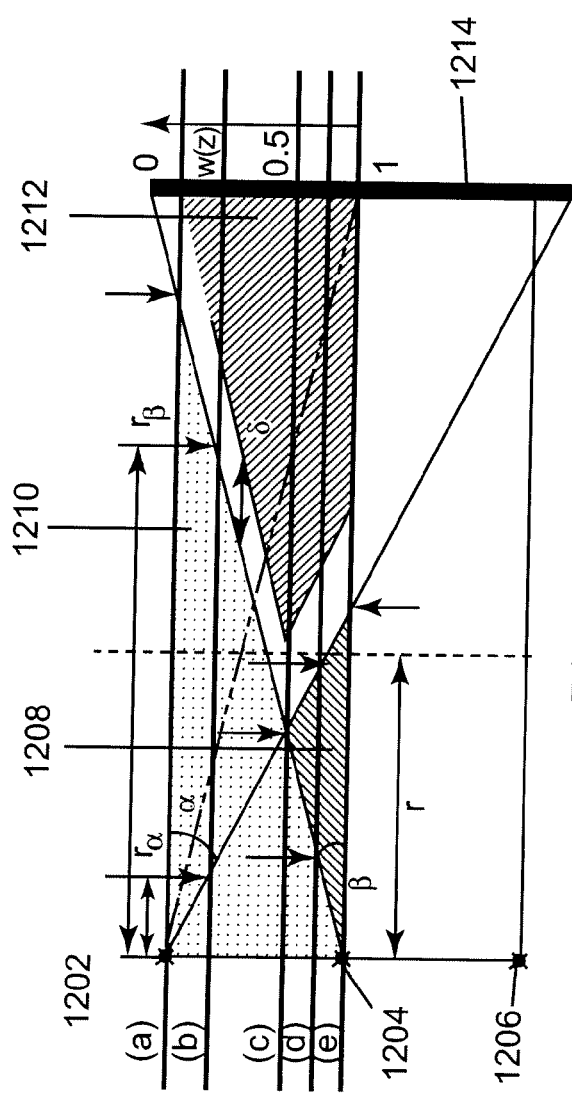
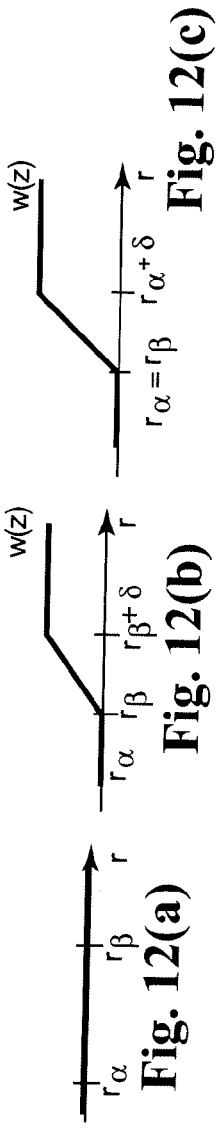
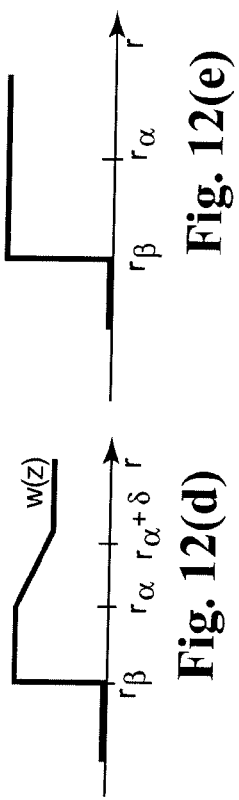
Fig. 12
Fig. 12(a)
Fig. 12(b)
Fig. 12(c)
Fig. 12(d)
Fig. 12(e)

METHOD FOR ANALYTIC RECONSTRUCTION OF CONE-BEAM PROJECTION DATA FOR MULTI-SOURCE INVERSE GEOMETRY CT SYSTEMS

STATEMENT REGARDING FEDERALLY SPONSORED RESEARCH & DEVELOPMENT

This invention was made with Government support under grant number EB006837 awarded by the National Institutes of Health. The Government has certain rights in the invention.

BACKGROUND

The invention relates generally to multi-source inverse geometry CT ("IGCT") systems and more particularly to a method and system for three-dimensional analytic reconstruction of cone-beam projection data, acquired using an IGCT system.

Most modern CT scanners are based on a third generation architecture, which embodies a single x-ray source and a large x-ray detector. The x-ray detector can be a one-dimensional, usually curved, array of detector cells, resulting in fan-beam geometry. In axial scans (i.e. the patient table does not move during the gantry rotation) the result is a purely planar dataset to which two-dimensional ("2D") filtered backprojection (FBP) can be applied. Reconstruction is theoretically exact, and any possible image artifacts may come from physical limitations of the scanner, such as quantum noise, aliasing, beam hardening, and scattered radiation.

In the early 1980's, helical (or spiral) CT systems were introduced. Such systems acquired data faster by translating the patient table during the gantry rotation. In a helical CT system, the raw CT data is typically interpolated to 2D planar datasets as if it was acquired without table translation, and 2D FBP is applied.

Since about 1990, multi-slice or multi-detector-row CT systems have become the standard CT architecture for premium medical scanners, wherein the detector has multiple rows, i.e. a two-dimensional array of detector cells, resulting in cone-beam geometry. Since these geometries do not result in planar datasets, 2D image reconstruction algorithms will not be based on the correct scan geometry and may result in cone-beam artifacts. For axial scan mode, Feldkamp, Davis, and Kress proposed a three-dimensional ("3D") cone-beam reconstruction algorithm ("FDK algorithm") that adapts 2D fan-beam filtered backprojection (FBP) to cone-beam geometry. The FDK algorithm works well near the mid-plane and near the center of rotation, but artifacts occur and get worse as the cone-angle increases. For 40 mm-coverage scanners (which typically corresponds to about a 4 degree cone-angle) significant artifacts occur, particularly towards the z=−20 mm and z=20 mm slices. The raw CT data is actually fundamentally incomplete in 3D axial scans, and therefore, even the best thinkable algorithm will result in artifacts in some cases.

On the other hand, in helical cone-beam scans, the data is fundamentally complete (provided the table speed is not too high compared to the gantry rotation speed and the slice thickness) and therefore exact reconstruction is possible. The FDK algorithm has been adapted for helical scan modes, but results in non-exact or approximate reconstruction. Accordingly, exact 3D helical cone-beam reconstruction algorithms ("Katsevitch algorithms") have been developed, which perform filtering operations along special filter lines followed by backprojection. Disadvantages associated with the Katsevitch algorithms are that such algorithms assume the detector surfaces are continuously sampled, and that such algorithms have other associated limitations.

Another disadvantage associated with the fan-beam and cone-beam geometries discussed above is that each type of geometry has a limited field of view ("FOV"). In a fan-based geometry, the FOV is an area of a scannable object that constantly receives an x-ray beam as the source and detector rotate around the scannable object. At some image voxels outside the FOV, the projection data is incomplete. Consequently, the size of the FOV and how many artifacts (if any) it contains are important, the goal being to make the FOV as large as possible and as free of as many artifacts as possible. In conventional CT systems, the size of the FOV is proportional to the trans-axial size of the x-ray detector. The larger the detector, the larger the FOV will be, and vice versa. Increasing the size of the detector makes the FOV larger but is technically difficult and costly to implement.

As an alternative to using a larger detector to cover the FOV, multi-source CT imaging systems have been developed wherein multiple sources sequentially project a part of the FOV onto a much smaller detector. Specifically, these systems typically use a small detector combined with a large distributed source, on which multiple x-ray sources are arrayed trans-axially (in the x-y-plane) and longitudinally (along the z-axis). Each x-ray source emits a fan-beam (or a cone-beam) at different times, and the projection data (e.g., sinograms) is captured by the detector. FIG. 1 is a three-dimensional perspective view of a multi-source inverse geometry CT (IGCT) system. As shown in FIG. 1, the system 100 includes a detector 101 combined with a large distributed x-ray source 102, on which multiple x-ray sources 103 are arrayed trans-axially (in the x-y-plane) and longitudinally (along the z-axis). Each x-ray source 103 emits a fan-beam (or a cone-beam) 104 at different times, and the projection data (e.g., sinograms) 105 is captured by the detector 101. Additionally, the detector 101, the distributed source 102, and the fan beams (or cone-beams) 104 may be axially rotated about a rotational axis 107. The projection data 105 captured by the detector 101 is processed to reconstruct an object of interest within the field of view 106. Trans-axially, the multiple x-ray sources 103 are positioned preferably on an iso-centered arc so that all corresponding fan beams (or cone beams) 104 can be rotated to fit into a conventional third generation system with an iso-focused detector. This makes exact re-binning to full cone beams possible and also helps to achieve a uniform beam profile. The resulting dataset can be re-arranged or re-binned into multiple longitudinally offset third-generation datasets. An algorithm developed for the multiple x-ray sources 103 distributed in z can also be applied to multiple longitudinally-offset axial scans with a conventional third generation CT system, and vice versa. While positioning the sources on iso-centric arcs is desirable for these reasons, other arrangements, such as detector-centered arcs and flat arrays, can also be used.

An embodiment of multi-source projection data re-binning is shown in FIGS. 2 and 3. In FIG. 2, a multi-source IGCT system 200 includes a single x-ray detector array 201 and a plurality of x-ray sources 203, which are arranged along an iso-centered arc at a predetermined radius from the x-ray detector 201. In use, each x-ray source 203 projects a beam 202, 204 onto the detector 201. Each beam 202, 204 creates a sinogram (not shown). Thus, as can be appreciated from FIG. 2, raw projection data from the multi-source IGCT system 200 comprises a group of sinograms that are generated by the x-ray sources 203.

In FIG. 3, a conventional third generation CT system 300 is shown that comprises a single x-ray source 303 positioned at a predetermined distance from at least two detector arrays 301 that are aligned along an iso-centered arc. Comparing FIGS. 2 and 3, it is seen that the beam 202 in the IGCT system 200 corresponds to the beam 302 in the third generation CT system 300, and that the beam 204 in the IGCT system 200 corresponds to the beam 304 in the third generation CT system 300. Consequently, sinograms that correspond to the beams 202, 204 in FIG. 2 and that are in the same trans-axial plane may be combined and re-arranged by a re-binning process. When each x-ray source 203 on the same trans-axial plane is positioned on the same iso-centered circle (e.g. shifted to the point occupied by the single point source 303 in FIG. 3), exact rebinning is possible. As FIG. 3 illustrates, the resulting re-binned sinogram will exactly correspond to a sinogram from a third generation system having multiple flat panel detectors 301 positioned along an iso-centered circle 306.

Multi-source IGCT 3D rebinning may use any of the following three techniques (or combinations thereof): (1) z-rebinning, (2) trans-axial (x-y) rebinning, and (3) feathering between sub-views, each of which is further described below.

The z re-binning technique re-bins the IGCT projection data for example to a source-focused-detector geometry. For example, each sinogram may be rebinned using 1D linear interpolation with extrapolation. Depending on the new source-to-iso-center distance, a larger detector height may be required to capture all the information.

The trans-axial (x-y) rebinning technique further rebins the IGCT projection data to a third generation geometry with a source-focused detector. To perform trans-axial rebinning, the angle and the distance from center for each ray are computed and interpolated into the desired geometry.

A process called "feathering" is used in situations where some mismatch may occur between measurements at the edge of the detector array across neighboring sub-sinograms. To mitigate this discontinuity, a slightly larger detector can be used, such that there is some overlap between neighboring sub-sinograms. The overlapping channels are multiplied with linearly decreasing/increasing weights and added together with the weighted channels from the adjacent sub-sinograms.

FIG. 4 illustrates multi-source IGCT projection data 401 that is re-binned and/or feathered to produce a re-binned third generation sinogram 402. After the re-binning described above has been performed, the resulting multiple third generation sinograms are associated with x-ray sources 103 offset along the z-axis (as illustrated in FIG. 5). Therefore, any conventional 3D cone-beam reconstruction algorithm—such as FDK—can be used to reconstruct each of the third generation datasets. With multiple sinograms from different sources in z-axis, combining this projection data results in better reconstructions as compared to a single third-generation dataset. This is especially true since cone beam artifacts due to data insufficiency may be reduced using additional information from longitudinally offset data.

While multi-source CT imaging systems can extend the axial scan coverage to a large extent, without sacrificing image quality due to cone-beam artifacts, image reconstruction is typically based on the fact that a full scan of data (i.e., based on a full rotation of the CT gantry) can be acquired from the multiple x-ray sources. However, when only less than a full scan of data is available, conjugate rays are not available, and depending on system geometry, there can even be a region in the reconstruction volume that does not get illuminated by any x-ray source for a given view angle.

It would be desirable to develop a method to mitigate cone-beam artifacts and increase scan coverage by combining information from longitudinally distributed x-ray sources without sacrificing image quality, when only less than a full scan of data is available. In addition, it would be desirable to develop a method and system for analytically reconstructing cone-beam projection data, by combining information from longitudinally distributed x-ray sources, when only less than a full scan data is available.

BRIEF DESCRIPTION

Embodiments of the present invention address these and other needs. In one embodiment, a method for analytically reconstructing a multi-axial computed tomography (CT) dataset, acquired using one or more longitudinally-offset x-ray beams emitted from multiple x-ray sources is provided. The method comprises acquiring one or more CT axial projection datasets, wherein the CT axial projection datasets are acquired using less than a full scan of data. The method further comprises reconstructing the CT axial projection datasets to generate a reconstructed image volume. The reconstruction comprises backprojecting one or more voxels comprising the multi-axial CT dataset, along one or more projection views, based upon a cone-angle weight determined for the voxels, wherein the cone-angle weight for the voxels is determined along a longitudinal direction.

In another embodiment, a method for analytically reconstructing a multi-axial computed tomography (CT) dataset, acquired using one or more longitudinally-offset x-ray beams emitted from multiple x-ray sources is provided. The method comprises acquiring one or more CT axial projection datasets, wherein the CT axial projection datasets are acquired from one or more longitudinally offset x-ray sources, using less than a full san of data. The method further comprises reconstructing the CT axial projection datasets to generate a reconstructed image volume. The reconstruction comprises backprojecting one or more voxels comprising the multi-axial CT dataset, based upon a cone-angle weight determined for the one or more voxels, wherein the cone-angle weight for the voxels is determined along a trans-axial plane.

DRAWINGS

These and other features, aspects, and advantages of the present invention will become better understood when the following detailed description is read with reference to the accompanying drawings in which like characters represent like parts throughout the drawings, wherein:

FIG. 2 is a diagram that illustrates a geometry of x-ray beams produced by multiple individual point x-ray sources in the multi-source IGCT system of FIG. 1;

FIG. 3 is a diagram that illustrates how projection data from the IGCT system of FIG. 2 may be exactly re-binned to correspond to the projection data obtained by a third generation CT system having only a single x-ray source and multiple x-ray detectors;

Figure 1:
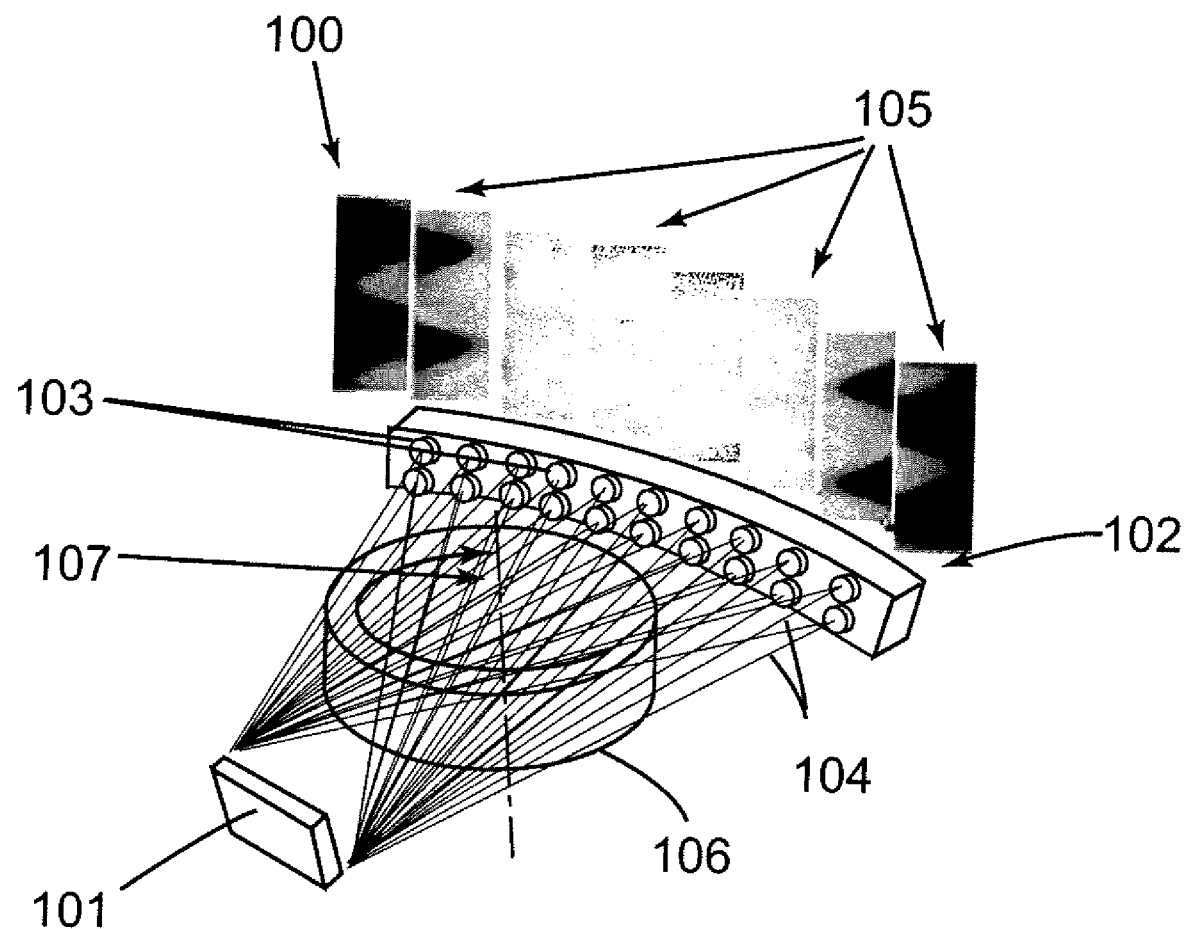
FIG. 1 is a three-dimensional perspective view of a multi-source IGCT system.
Figure 5:
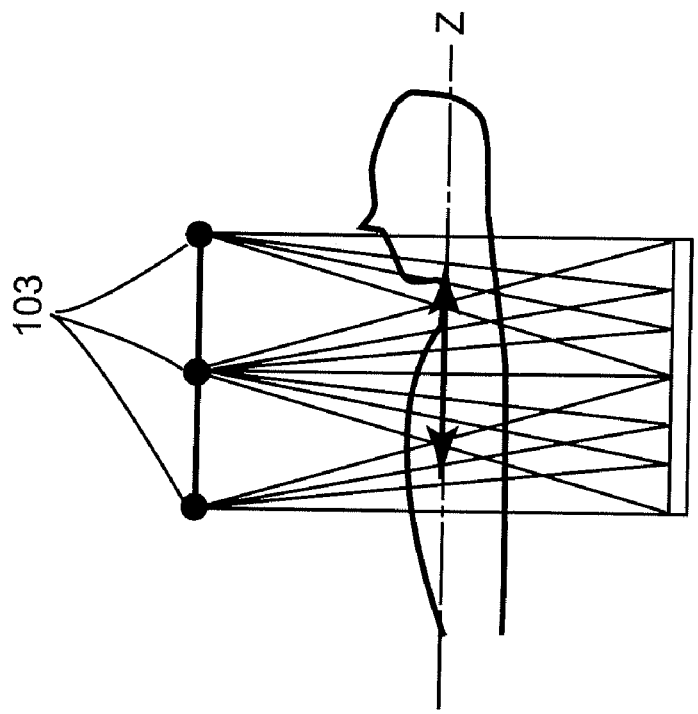
Figure 4:
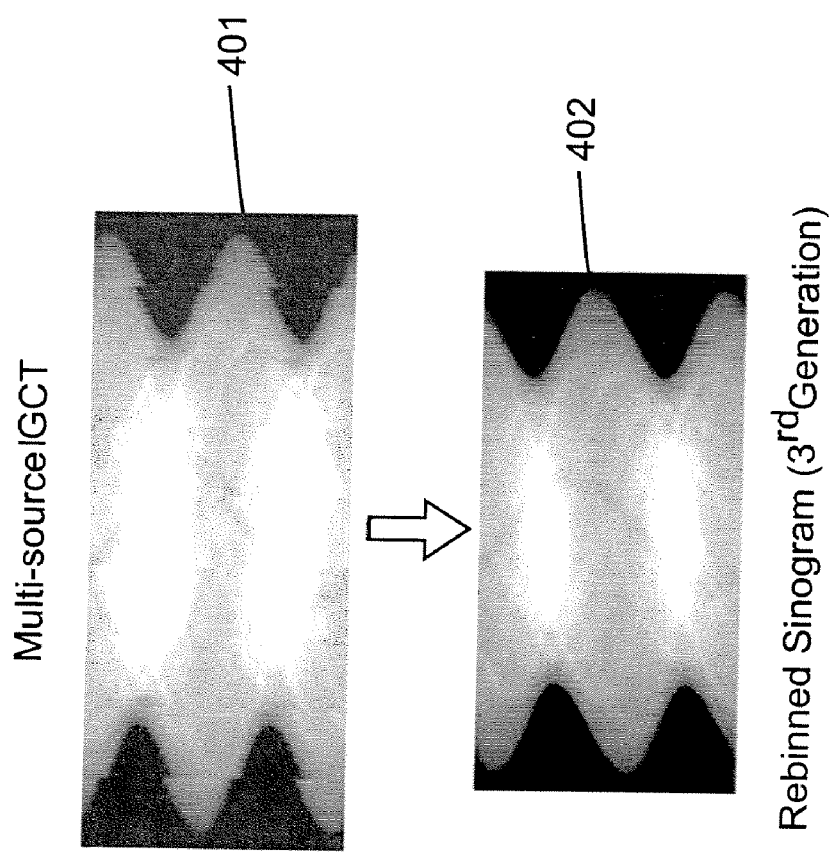
Figure 6:
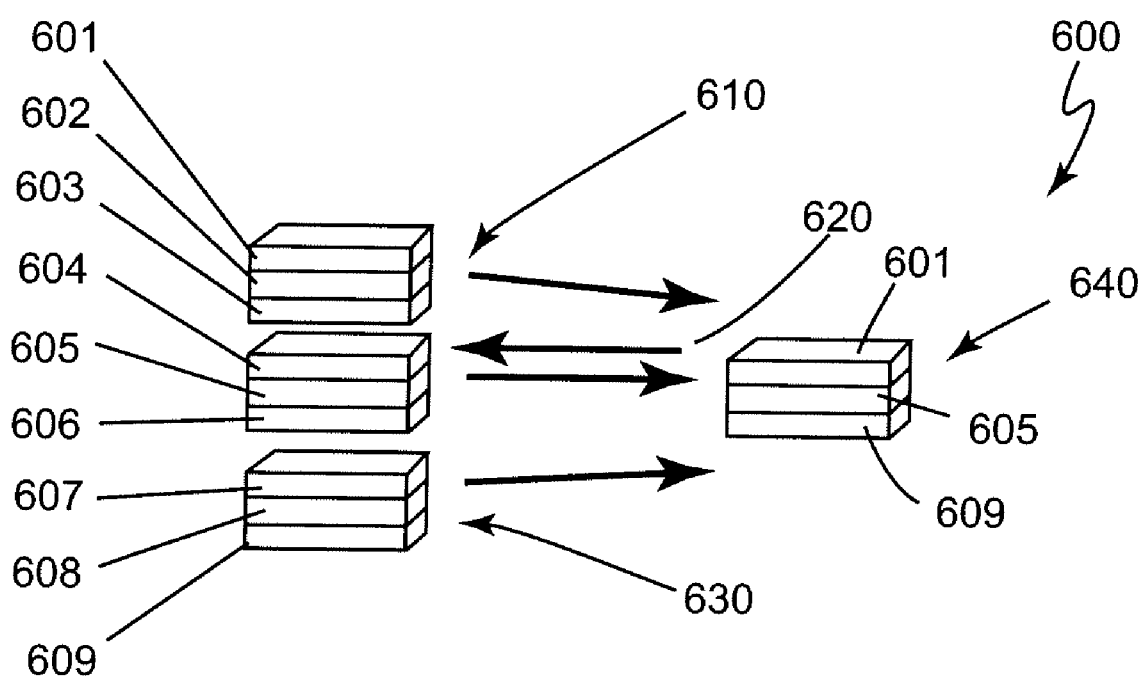
Figure 9:
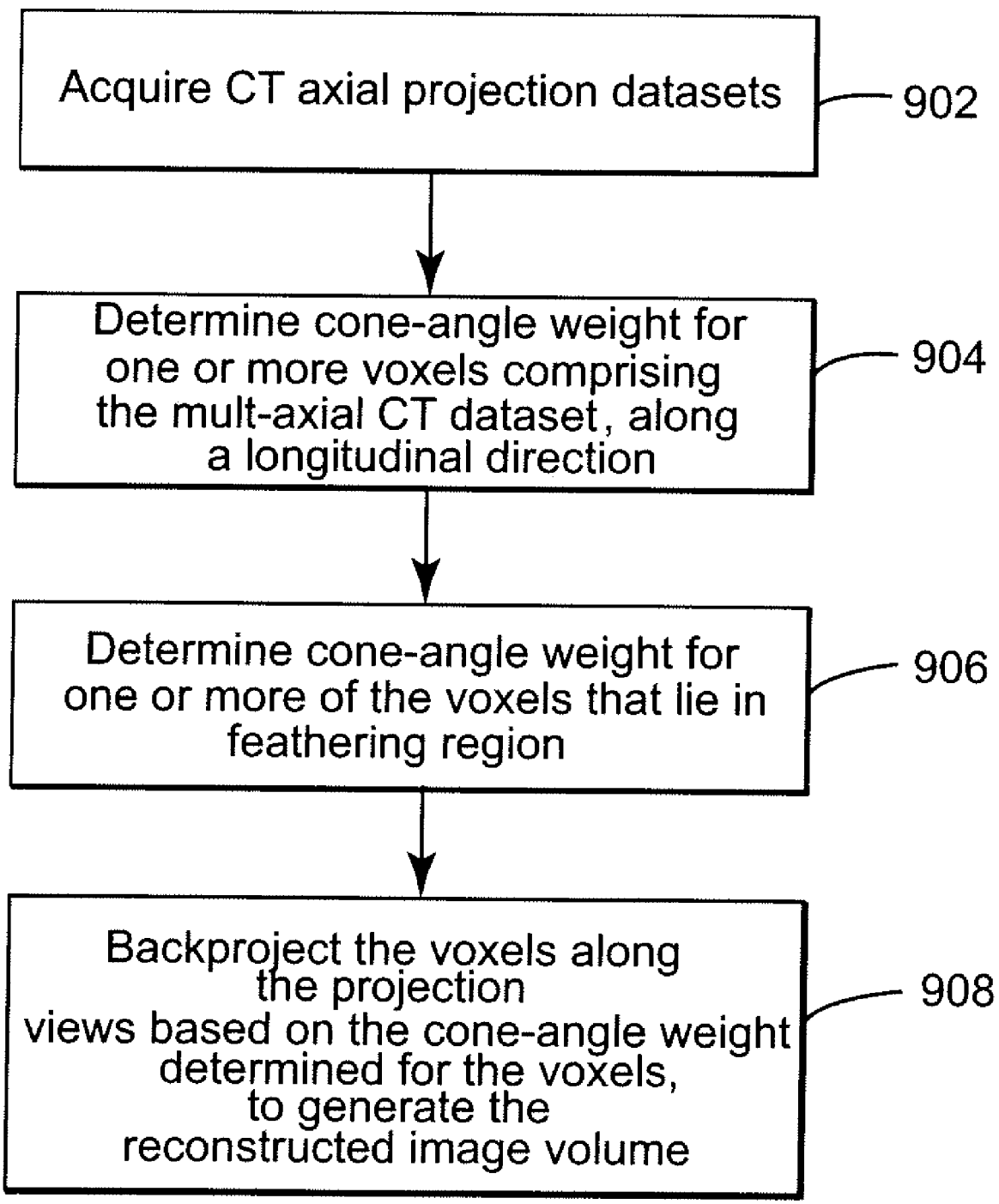
Figure 10:
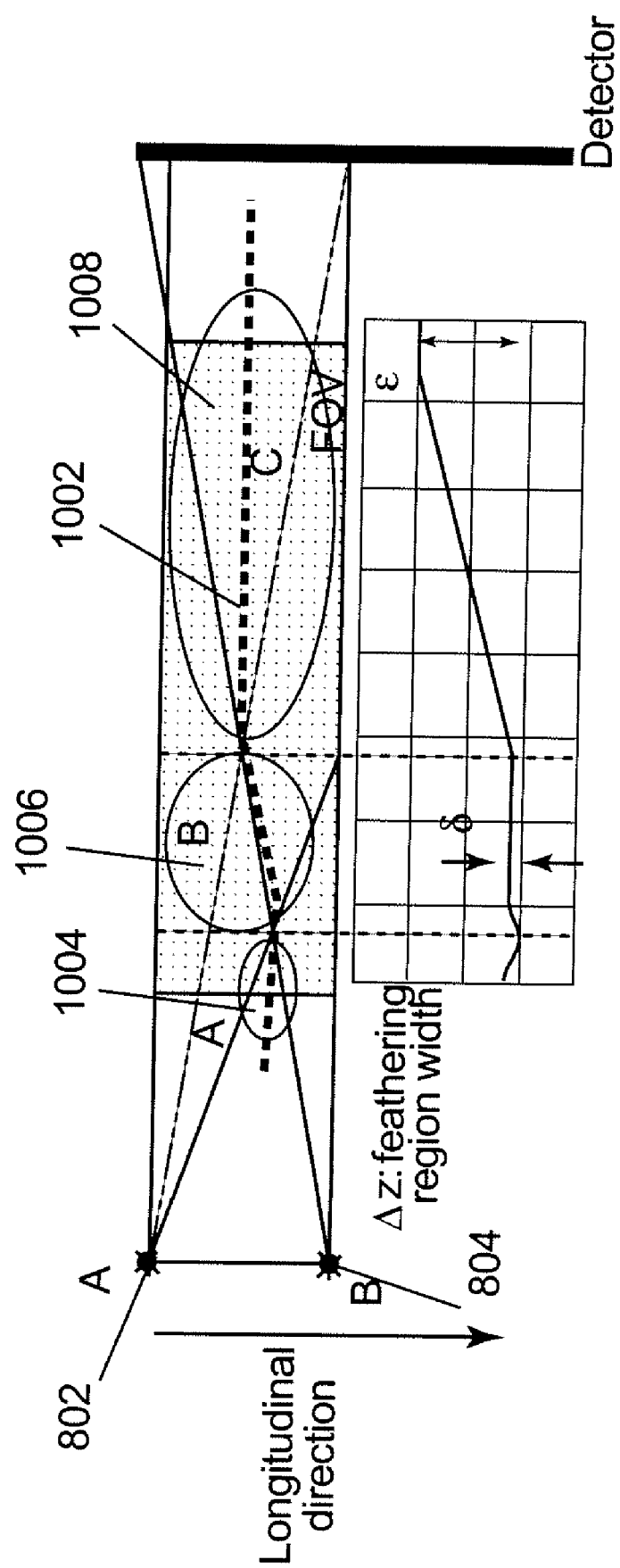
Figure 11:
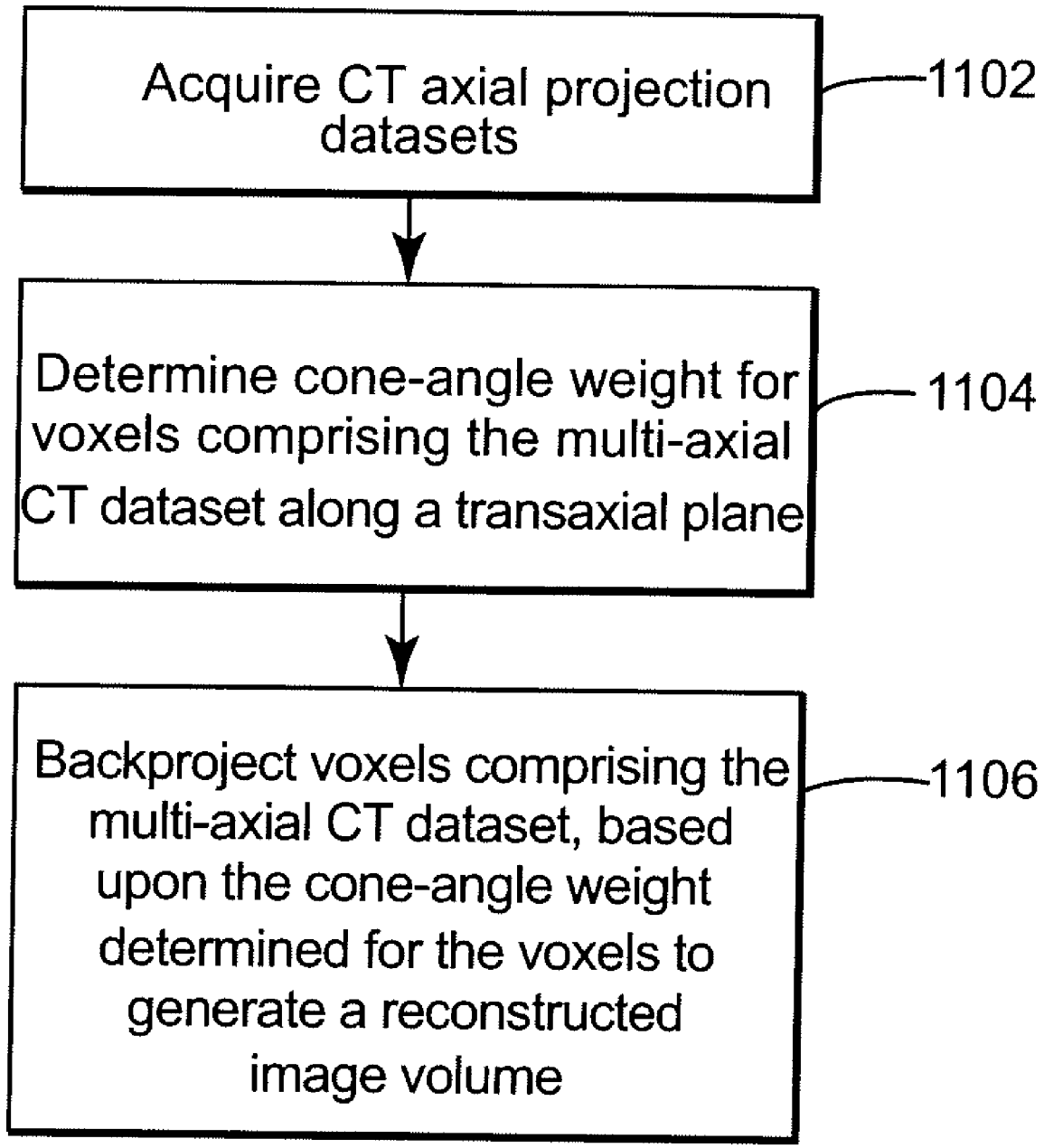
Figures 13A, 13B:
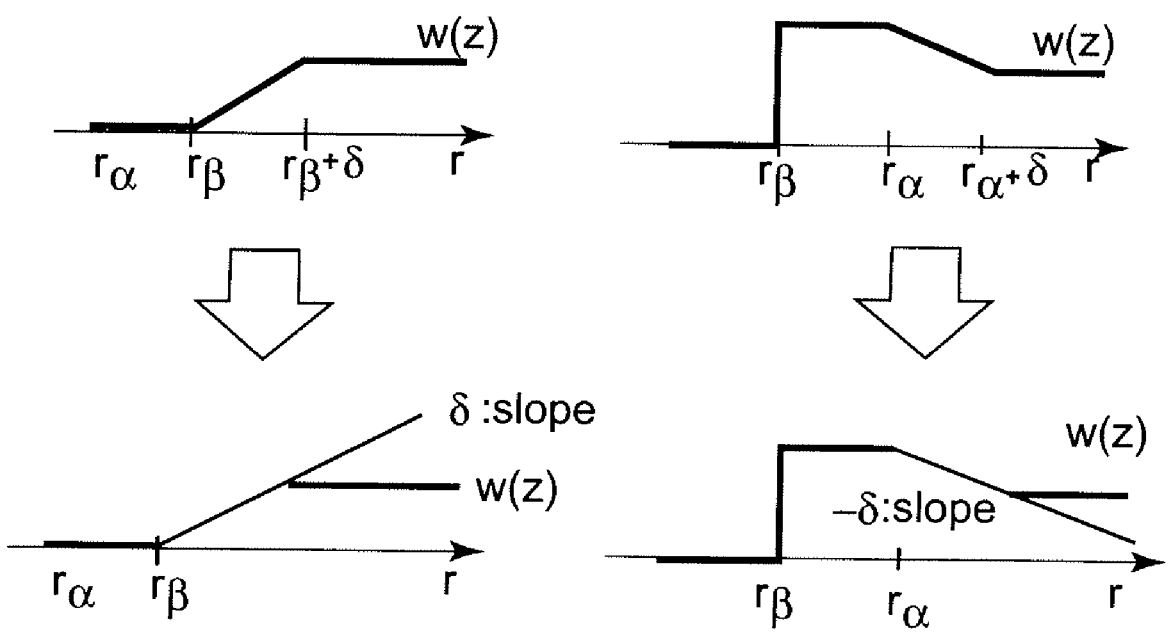
Figure 14:
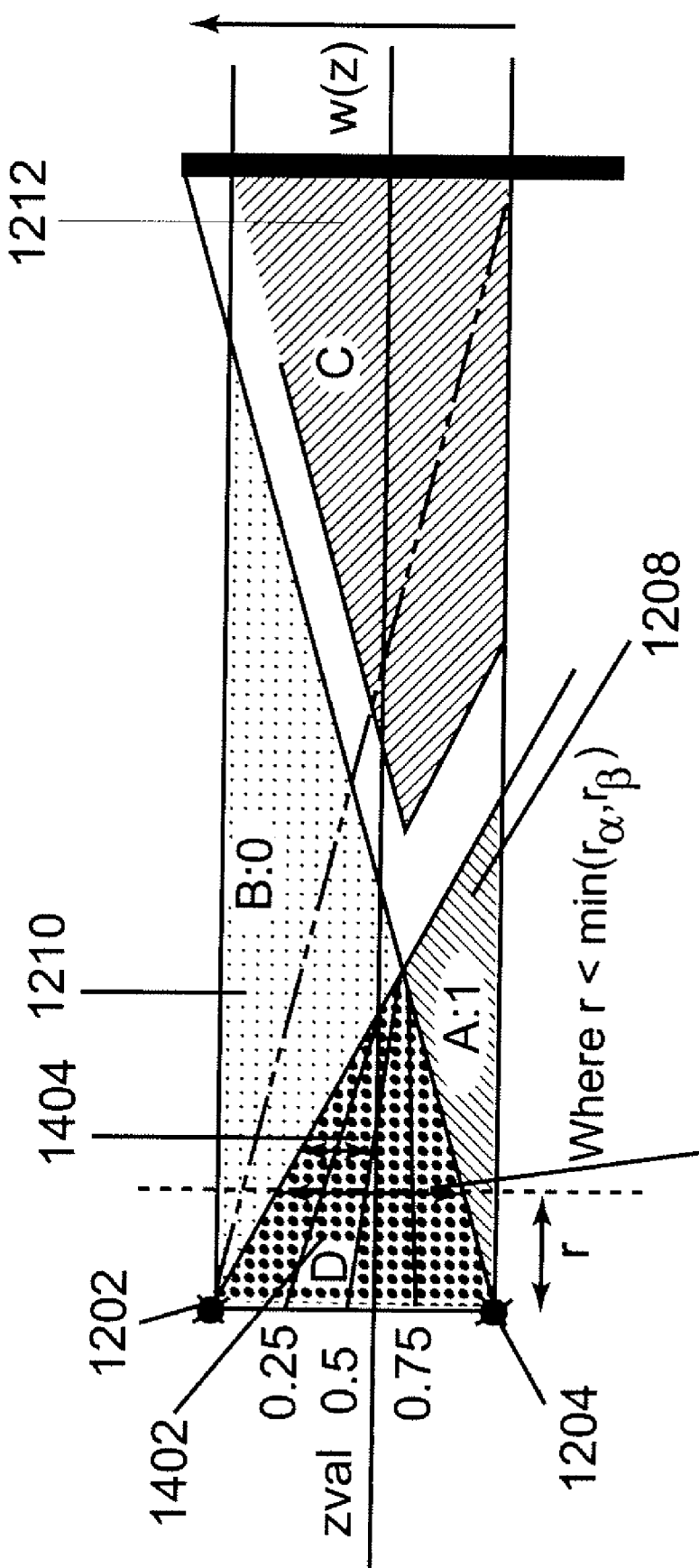

FIG. 4 includes two diagrams, one of which represents raw multi-source IGCT data, the other of which represents the multi-source IGCT projection data after a rebinning operation;

FIG. 5 is a diagram illustrating how the re-binned multi-source IGCT projection data of FIG. 4 can be associated with x-ray sources offset along the z-axis and thereafter reconstructed using a conventional 3D cone-beam reconstruction algorithm;

FIG. 6 is a diagram illustrating a method for performing reconstruction of multi-slice IGCT image data;

FIG. 7(*a*) illustrates an exemplary missing data region present in a reconstructed volume of a scanned object, for one or more projection datasets acquired using a full scan of data;

FIG. 7(*b*) illustrates an exemplary missing data region present in a reconstructed volume of a scanned object, for one or more projection datasets acquired using less than a full scan of data;

FIG. 8 is an exemplary illustration of how the cone-angle typically changes between multiple longitudinally offset x-ray sources, when only less than a full scan of data is available;

FIGS. 8(*a*)-8(*c*) illustrate graphically, how the cone-angle typically changes between longitudinally offset x-ray sources within various data regions in the reconstructed image volume corresponding to a scanned object;

FIG. 9 illustrates a technique for analytically reconstructing a multi-axial computed tomography (CT) dataset, acquired using one or more longitudinally offset x-ray beams emitted from multiple x-ray sources, in accordance with one embodiment of the present invention;

FIG. 10 illustrates a feathering region and associated feathering region widths, defined along a longitudinal direction, for a plurality of voxels comprising the reconstructed image volume;

FIG. 11 illustrates a technique for analytically reconstructing a multi-axial computed tomography (CT) dataset, acquired using one or more longitudinally offset x-ray beams emitted from multiple x-ray sources, in accordance with another embodiment of the present invention;

FIG. 12 illustrates exemplary data regions in a reconstructed image volume corresponding to a scanned object, and the computation of weights for voxels that lie in a radial direction along the trans-axial plane in the reconstructed image volume;

FIGS. 12(*a*)-12(*e*) illustrate graphically, how the voxel weights are computed for various image slices in the reconstructed image volume, corresponding to a scanned object;

FIGS. 13(*a*)-13(*b*) illustrate graphically, how the voxel weights are computed for various image slices in the reconstructed image volume, based on a fixed transition slope; and FIG. 14 illustrates an exemplary data region in a reconstructed image volume corresponding to a scanned object, and the computation of weights for voxels that lie in this region.

DETAILED DESCRIPTION

Embodiments of the present invention disclose techniques for analytically reconstructing cone beam projection datasets obtained from multiple longitudinally offset x-ray sources, in an IGCT system. In particular, embodiments of the present invention disclose techniques for efficiently combining one or more cone beam projection datasets from multiple longitudinally offset x-ray sources, to produce accurate reconstructions of an image object, when only less than a full scan of data is available for reconstruction.

One technique for combining projection datasets obtained from multiple longitudinally offset x-ray sources, from an IGCT system (as shown in FIG. 2), is to reconstruct desired image slices for one or more longitudinally offset x-ray sources and then combine the reconstructed slices to generate a reconstructed image volume. FIG. 6 illustrates a technique for combining information from one or more longitudinally distributed x-ray sources. Referring to FIG. 6, image slices 601, 602, 603, 604, 605, 606, 607, 608, and 609 corresponding to each projection dataset (each x-ray source, z location) are reconstructed, with one set of slices (or reconstructed volume) for each dataset. Each dataset 610, 620, 630 comprises three sets of slices. For example, a first dataset 610 comprises slices 601, 602, and 603. A second dataset 620 comprises slices 604, 605, and 606. A third dataset 630 comprises slices 607, 608, and 609. These three datasets are then combined by selecting the best respective slices from each of the three sets or by applying a weighted average. For example, with three x-ray sources along the z-axis, the reconstruction from the center source will suffer from cone-beam artifacts at the top slices and the bottom slices. But the reconstruction volume from the top source will provide artifact-free top slices, and analogous for the bottom source. So essentially, in this embodiment, for every z-position, the best slices 601, 605,609 from the three reconstruction volumes associated with each x-ray source are chosen and combined into a single volume 640.

As will be appreciated by those skilled in the art, when only less than a full scan of data is available for reconstruction, combining data from multiple longitudinally offset x-ray sources, is not straight forward, because now the reconstruction volume is divided into several regions, i.e., regions with no illumination and/or regions that get illuminated several times. FIG. 7(*a*) illustrates an exemplary missing data region present in a reconstructed volume of a scanned object, for one or more projection datasets acquired using a full scan of data. FIG. 7(*b*) illustrates an exemplary missing data region present in a reconstructed volume of a scanned object, for one or more projection datasets acquired using less than a full scan of data. For a full scan collimation, as shown in FIG. 7(*a*), conjugate rays may be used to cover the missing data region 702 in the reconstructed image volume. That is, scan data generated from the multiple x-ray sources 103 provide complementary information based on the conjugate rays, to cover the missing data region, 702, in the reconstructed image volume. However, when only less than a full scan of data is available, as shown in FIG. 7(*b*), the size of the missing data region 704 cannot be covered since triangular patching of conjugate data from the longitudinally offset x-ray sources 103 is no longer possible. One way to reduce the size of this missing data region is to open up the collimators for one or more of the x-ray sources 103, to increase the longitudinal extent of the x-ray beams. For example, as shown in FIG. 7(*b*), the top and bottom collimators 705, 706 for the x-ray sources, 103 are opened up to increase the longitudinal extent of the x-ray beams. However, when the collimators are opened up, asymmetric cone-angles occur between x-ray source transitions, resulting in asymmetric behavior around transition slices. Hence, transition slices have poor image quality since they have larger cone-angles compared to other image slices.

Furthermore, when only less than a full scan of data is available for reconstruction, some voxels may not get illuminated from any x-ray source at all and transitions between multiple x-ray sources may result in artifacts due to data inconsistencies. Referring to FIG. 8 now, an exemplary illustration of how the cone-angle typically changes between multiple longitudinally offset x-ray sources, when only less than a full scan of data is available, is illustrated. FIG. 8 further illustrates three data regions 806, 810 and 812 in the reconstructed image volume, along the longitudinal direction (z-direction). These regions 806, 810 and 812 are further graphically illustrated in FIG. 8(*a*), FIG. 8(*b*) and FIG. 8(*c*) respectively. As may be observed from the graph shown in FIG. 8(*a*), for voxels that lie in a data region 806, a cone-angle does not get detected from either of the x-ray sources, 802, 804, resulting in missing data. Similarly, from the graph shown in FIG. 8(b), it may be observed that for voxels that lie in the data region 810, data is not available from x-ray source 802, but data from x-ray source 804 is available, resulting in data discontinuities due to the presence of asymmetric cone-angles. The graph shown in FIG. 8(c) illustrates an ideal scenario when the cone-angles from both the x-ray sources are the same, resulting in a smooth data transition.

In order to reduce artifacts from missing data when only less than a full scan of data is available, an extrapolation in z to each dataset prior to reconstruction (i.e., prior to back-projection) may be performed. This step may be incorporated into a multi-source rebinning process as described above, by replicating the top and bottoms rows in the original dataset until the desired field of view is fully covered, and rebinning to a bigger detector. Further, in order to avoid sudden changes along the z direction, the transition from one x-ray source to the next may be performed gradually, by feathering their relative weights across a few transition slices. As will be described in greater detail below, in order to minimize discontinuities along the longitudinal direction and still achieve good image quality, embodiments of the present invention disclose efficient techniques for combining data obtained from multiple longitudinally offset x-ray sources using a view-based weighting approach that is applied to one or more voxels in the reconstructed image volume.

FIG. 9 illustrates a technique for analytically reconstructing a multi-axial computed tomography (CT) dataset, acquired using one or more longitudinally offset x-ray beams emitted from multiple x-ray sources, in accordance with one embodiment of the present invention. In step 902, one or more CT axial projection datasets are acquired, using for example, the IGCT system described in FIG. 2 above. In one embodiment, the CT axial projection datasets are acquired using less than a full scan of data (i.e., using a less than full rotation of the CT gantry). Further, in one embodiment, the multi-axial CT dataset comprises cardiac image data corresponding to a scanned object.

In step 904, a cone-angle weight for one or more voxels comprising the multi-axial CT dataset is determined along a longitudinal direction (z-direction). In one embodiment, the cone-angle weight for each voxel is determined by identifying at least one x-ray source illuminating a voxel being back-projected. In a particular embodiment, each voxel in the reconstructed volume is assigned a different weight that is multiplied for each projection view being backprojected, wherein the weight for each voxel is determined based upon the cone-angle associated with the x-ray source that contributes to the illumination of a voxel. In other words, for each projection view, each voxel in the reconstruction volume identifies at least one longitudinal x-ray source to be back-projected, with a weight that is determined based upon the cone-angle associated with the x-ray source that contributes to the illumination of the voxel. For example, if only one x-ray source contributes to the illumination of a voxel, a binary weighting for the voxels is applied. For voxels that select more than one x-ray source to be backprojected, a non-binary weighting, depending on the cone-angle associated with the x-ray source, is applied. In other words, a voxel is assigned a weight of "one" if only one x-ray source contributes to the illumination of the voxel and assigned a weight of "zero" when no x-ray source contributes to the illumination of the voxel. When two x-ray sources contribute to the illumination of a voxel, a partial contribution is determined depending on the cone-angle associated with the x-ray sources, such that for a zero cone angle, a voxel is assigned a weight of "one" and as the cone angle increases, the voxel weights gradually decrease to zero.

Further, and in one embodiment, a feathering region is defined along the longitudinal direction (z-direction) between one or more x-ray source transition points in order to minimize discontinuities along the longitudinal direction and still achieve cone-angle dependent weighting for the voxels that lie in the feathering region. As used herein, a "transition point" refers to a data point (or an image slice) in the reconstructed image volume corresponding to a scanned object, where a transition between the longitudinally offset x-ray sources occurs. Accordingly, in step 906, a cone-angle weight is determined for one or more of the voxels that lie in the feathering region. In one embodiment, the cone-angle weight for a voxel that lies in the feathering region is determined based on identifying the cone-angles associated with the x-ray sources that contribute to the illumination of the voxel, in the feathering region. For example, when each x-ray source contributes equally (for e.g., 50%) to the backprojection of a voxel along a projection view, the center of the feathering region, is determined by selecting the region where the cone-angles from the two x-ray sources are the same if both the x-ray sources are available or along the outer most beam if only one x-ray source is available.

FIG. 10 illustrates a feathering region and associated feathering region widths, defined along a longitudinal direction, for a plurality of voxels comprising the reconstructed image volume. When both the x-ray sources 802 and 804 contribute to the illumination of a voxel, such as, for voxels that lie in region 1008, a 50% transition occurs at the center of the feathering region, 1002, which represents the location where the cone-angles associated with the two x-ray sources are equal. For voxels that lie in region 1008, the feathering region width varies, since it is desirable to average the data as much as possible and to the extent of data availability. However, when either only one x-ray source illuminates a voxel or even though two x-ray sources illuminate a voxel, only one x-ray source has a favorable cone-angle, such as for voxels that lie in region 1006, the transition always occurs along the favorable x-ray source. In this case, it is desirable to use the favorable x-ray source as much as possible. It may be noted that for voxels that lie in region 1006, the feathering region width is fixed and small since weights have to be reduced for voxels that are not illuminated by an x-ray source. When only one x-ray source illuminates a voxel or no x-ray source illuminates a voxel as for voxels that lie in region 1004, the feathering region is defined in the region where no information is available, preferably at the center between the two outmost beams from the two x-ray sources because extrapolated data is equally uncertain regardless of the cone-angle.

Further, and in one embodiment, one or more parameters may be selected to determine the transition points between the x-ray sources and the feathering region width, in order to achieve good reconstruction image quality. Referring to FIG. 10 now, $\delta$ represents the minimum feathering region width when transitions occur between x-ray sources and $\epsilon$ represents the maximum feathering region width when both x-ray sources are equally available and their cone angles are comparable. It may be noted that when the value of $\epsilon$ is small, the view-based cone-angle dependent weighting technique discussed above approaches a slice-based technique, which has uniform weighing throughout each slice, when data is aggressively extrapolated to reduce the missing data region volume. When the value of $\delta$ is a small, sharp transitions in the trans-axial plane occur and this results in small but very high contrast artifacts. A large value for $\delta$ on the other hand, will result in a smooth transition along the trans-axial plane but information from an unfavorable x-ray source associated with a higher cone-angle, may increase the occurrence of cone-beam artifacts.

In other words, when the value of δ is very small, the feathering region also becomes small and the weights along the longitudinal direction are not smooth, yielding small but very high contrast artifacts near image slices. When the value of δ is very large, the feathering region also becomes large. Since, a feathering operation is basically performed to determine the weighted average between adjacent rays from adjacent x-ray sources, when the feathering region is very large, unwanted information from the x-ray source with a bigger cone angle may be averaged, resulting in an image that suffers from residual cone beam artifacts. On the other hand, when the value of ε is very small, transitions only occur in a very narrow region and will not yield smooth transitions. Furthermore, since only a very narrow band of cone angles are considered, available information is not utilized efficiently, thereby resulting in cone-beam artifacts.

Referring to FIG. 9 again, in step 908, the voxels are backprojected along the projection views based on the cone-angle weight determined for the voxels as described in steps 904 and 906 above, to generate the reconstructed image volume.

As discussed above, continuity along the longitudinal direction (z-direction) may be achieved by feathering along the same direction. However, this does not guarantee the continuity along the trans-axial x-y plane, since the trans-axial continuity is quite sensitive to changes in the value in δ, wherein δ represents the feathering region width for transitions between x-ray sources. In accordance with another embodiment of the present invention, continuity is achieved along the radial direction, i.e., in the direction from the source to detector on any given reconstruction slice.

In one embodiment, and as will be discussed in greater detail below, to achieve continuity along the trans-axial direction, the reconstruction volume is divided into several regions with fixed weights and cone-angle dependent weights. A region where a given x-ray source illuminates a voxel is assigned a weight of one and a region where no x-ray source illuminates a voxel is assigned a weight of zero. A region where two x-ray sources illuminate a voxel is assigned a variable weight depending on its longitudinal location. If the location of a voxel is in a region in a direction along the x-ray source, the voxel weight of one is assigned, and the weight gradually decreases as the cone angle increases. When a voxel converses along the trans-axial direction, it passes through these various regions and whenever a transition occurs, a linear interpolation between two regions takes place, with either a fixed region width δ or a fixed transition rate δ, as will be described in greater detail below.

FIG. 11 illustrates a technique for analytically reconstructing a multi-axial computed tomography (CT) dataset, acquired using one or more longitudinally offset x-ray beams emitted from multiple x-ray sources, in accordance with another embodiment of the present invention. In step 1102, one or more CT axial projection datasets are acquired, using for example, the IGCT system described in FIG. 2 above. In one embodiment, the projection datasets are acquired using less than a full scan of data (i.e., using a less than full rotation of the CT gantry). Further, in one embodiment, the multi-axial CT dataset comprises a cardiac dataset corresponding to a scanned object.

In step 1104, a cone-angle weight for one or more voxels comprising the multi-axial CT dataset is determined along a trans-axial plane (x-y plane). In one embodiment, the cone-angle weight for the voxels that lie in a radial direction along the trans-axial plane is determined, by identifying at least one x-ray source that contributes to the illumination of the voxels. In a particular embodiment, and as discussed in greater detail with respect to FIG. 12 and FIG. 13 below, the cone-angle weight for the voxels along the trans-axial plane is determined based on identifying the cone-angles associated with the one or more the x-ray sources that contribute to the illumination of the one or more voxels, along the trans-axial plane.

In step 1106, the voxels comprising the multi-axial CT dataset are backprojected, based upon the cone-angle weight determined for the one or more voxels, to generate a reconstructed image volume.

Referring to FIG. 12 now, exemplary data regions are illustrated within a reconstruction volume corresponding to a scanned object. As may be observed from FIG. 12, voxels that lie in region 1208 get illuminated by the given x-ray source, voxels that lie in region 1210 do not get illuminated by any x-ray source and voxels that lie in region 1212 get illuminated by more than one x-ray source. In one embodiment, a weight of one is assigned to the voxels that lie in region 1208, and a weight of zero is assigned to the voxels that lie in region 1210. In other words, image slices that lie closer to the center plane are assigned voxel weights that approach a value of one and image slices that move forward to the edge of the detector, 1214, are assigned weights that approach a value of zero. For voxels that lie in region 1212, the voxel weight is determined by considering the cone-angle associated with the x-ray sources that contribute to the illumination of the voxel.

Further, each voxel in the reconstruction volume may be uniquely represented by its radial location and longitudinal location at a given fan angle. As shown in FIG. 12, 'r' represents the radial location of a given voxel point in the reconstruction volume and $r_\alpha$ represents the distance from the x-ray source 1204 to the intersection between a given image slice and the cone-beam corresponding to the x-ray source 1202, wherein α refers to the maximum cone-angle. Similarly, $r_\beta$ represents the distance from the x-ray source 1204 to the intersection between a given image slice and the cone-beam from the x-ray source 1204, wherein β represents the maximum cone-angle. The feathering region width for transition between the image slices is represented by δ.

In one embodiment, a smooth transition between the regions 1208, 1210 and 1212 is performed by defining a fixed feathering region width, and a fixed slope with a variable feathering region, as will be described in greater detail below.

FIG. 12 also illustrates the computation of weights for voxels that lie in a radial direction along the trans-axial plane in the reconstructed image volume. In one embodiment, the voxel weights are computed with respect to x-ray source 1204. For voxels that lie in region 1210, the voxel weight is zero until r reaches $r_\beta$. For voxels that lie in region 1208, the voxel weight is one since r is bigger than $r_\beta$ and smaller than $r_\alpha$. As illustrated by the graph shown in FIG. 12(a), for image slice (a), the x-ray source 1204 does not contribute to the illumination of a voxel and hence the voxel weights are zero for all values of r. For image slice (b), and as illustrated by the graph shown in FIG. 12(b), the transition between regions 1210 to 1212 occurs, so the weight changes from zero to w(z) depending on the longitudinal location of a given voxel, wherein w(z) refers to a linear function that varies from one to zero when z varies from zero to half the detector height. In mathematical form, $w(z)=-z/h+1$, where h is half the detector height.

Image slice (c) is similar to image slice (b), as illustrated in the graph shown in FIG. 12(c), except when the value of $r_\alpha = r_\beta$. In the case of image slice (d), and as illustrated by the graph shown in FIG. 12(d), the transition occurs through region 1210 to region 1208 and to region 1212, so the weights change from zero to one and decrease along w(z). For image slice (e), and as illustrated by the graph shown in FIG. 12(e), the x-ray source 1204 contributes 100% to the illumination of the voxel, so the voxel weight is one for all values of r.

In one embodiment, the transition duration remains fixed. The fixed transition duration implies a specific feathering width, regardless of the extent of transition. In another embodiment, the transition rate may also be fixed, as illustrated further in the graphs shown in FIG. 13(a) and FIG. 13(b).

As noted above, smooth transitions between voxel weights may be achieved by either having a fixed transition duration or a fixed transition rate. In one embodiment, the width of the feathering region is fixed so that the starting weights gradually increase or decrease to reach an ending weight in a fixed interval. If the difference between the starting weights and ending weights is large, transitions can occur suddenly because of a fixed duration, thereby resulting in data discontinuities. In another embodiment, and as shown in FIGS. 13(a) and 13(b), the transition rate of the feathering region may be fixed so that the starting weight gradually increases or decreases to reach the ending weight in the same speed. Now if the difference between the starting and ending weights is large, transition takes place in a longer duration, thereby yielding a smoother change.

Continuing with the discussion of FIG. 12 above, there also exists a region in the reconstructed image volume corresponding to a scanned object, wherein voxels are not illuminated by any x-ray source. FIG. 14 illustrates a region in the reconstructed image volume, wherein voxels are not illuminated by any x-ray source. In one embodiment, the weights for voxels that lie in region 1402 may be determined by extrapolating the data in this region. Referring to FIG. 14, the ratio between the distance from the current z-value to the cone-beam associated with a maximum cone-angle from the x-ray source 1202 is represented by the reference numeral 1404 and the total longitudinal region width at a given radial location r is represented by the reference numeral 1406.

As may be observed, the contributions from the extrapolated data from the x-ray source 1204 gradually decrease towards x-ray source 1202 and eventually fall to zero. In one embodiment, the weight of a voxel that lies in this region may be computed based on the proximity of a given voxel to the outmost ray from a given x-ray source. In a particular embodiment, the weight of a voxel that lies in this region is computed as a ratio between the longitudinal size of the region 1406, at a given radial position, and the longitudinal distance from the given slice to the upper limit of the region, 1404.

The technique discussed above, while achieving continuity along the trans-axial plane, results in the scarce sampling of data along the longitudinal direction and eventually results in data discontinuities both in the longitudinal direction as well as the trans-axial direction. Accordingly, and in one embodiment of the present invention, an over-sampling of the scanned data in the longitudinal direction (z-direction) may be performed to avoid data discontinuities in the trans-axial plane, wherein the sampled data is averaged before computing voxel weights, resulting in the generation of a reconstructed image volume with fewer artifacts. In one embodiment, weights are computed for twice the number of slices and then smoothed before multiplying during backprojection.

Embodiments of the present invention disclose efficient techniques for mitigating cone-beam artifacts and increasing scan coverage without scarifying image quality, by combining information from longitudinally distributed x-ray sources, when only less than a full scan of data is available. Further, embodiments of the present invention disclose efficient techniques for combining one or more cone beam projection datasets from multiple longitudinally offset x-ray sources, to produce accurate reconstructions of an image object, when only less than a full scan of data is available for reconstruction. Further, embodiments of the present invention may be applied in radiology applications to generate reconstructed cardiac images with good temporal resolution.

Definitions: The following terms, as used herein, may comprise at least the following non-limiting definitions.

Longitudinally—aligned in the direction of a rotation axis; illustratively, along a z-direction Trans-axially—across two-dimensions and/or in a plane (x-y-plane) perpendicular to the rotation axis (illustratively, the z-axis).

Fan-beam geometry—$3^{rd}$ generation CT geometry with a single x-ray source and linear array (1D) detector.

Cone-beam geometry—$3^{rd}$ generation CT geometry with single x-ray source and multi-row (2D) detector.

Axial scan—a rotational scan without movement of a patient table.

Helical scan—a rotational scan with movement of a patient table.

Re-binning—the re-arrangement of a dataset corresponding to a new acquisition geometry or coordinated system.

Feathering—gradually changing a weighting or contribution of two partially overlapping datasets to achieve a smooth transition between them.

Iso-centered arc—an arc whose center lies on the rotation axis of a CT scanner

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for analytically reconstructing a multi-axial computed tomography (CT) dataset, the method comprising:
    simultaneously acquiring two or more CT axial projection datasets using multiple longitudinally offset X-ray sources, wherein each CT axial projection dataset comprises a half-scan of axial data; and
    reconstructing the two or more CT axial projection datasets to generate a reconstructed image volume using respective weights determined for one or more voxels of the image volume, wherein each respective the weight is determined based on at least two factors, wherein the first factor comprises a cone angle for the respective voxel determined primarily along the z-axis and wherein the second factor comprises a degree of redundancy attributable to a voxel being separately illuminated by different longitudinally offset X-ray sources in two or more of the CT axial projection datasets.

2. The method of claim 1, wherein the CT axial projection datasets are acquired using an Inverse Geometry Computed Tomography (IGCT) system.

3. The method of claim 1, wherein the weight for the one or more voxels is determined based upon identifying at least one x-ray source that contributes to an illumination of the one or more voxels being back projected.

4. The method of claim 3, wherein the weight for the one or more voxels is determined based upon identifying a cone-angle associated with the one or more x-ray sources that contribute to the illumination of the one or more voxels.

5. The method of claim 4, wherein determining the weight for the one or more voxels comprises applying a binary weight to the one or more voxels that are illuminated by a single x-ray source and applying a non-binary weight to the one or more voxels that are illuminated by a plurality of x-ray sources, based on the cone-angle associated with the x-ray sources.

6. The method of claim 3, further comprising determining a weight for one or more of the voxels that lie in a feathering region, between one or more x-ray source transition points.

7. The method of claim 6, wherein the weight for the one or more voxels that lie in the feathering region is determined based on identifying the cone-angles associated with the one or more of the x-ray sources that contribute to the illumination of the one or more voxels, in the feathering region.

8. The method of claim 7, wherein the feathering region is defined along a longitudinal direction between the one or more x-ray source transition points.

9. The method of claim 1, wherein the multiple x-ray sources distributed at least longitudinally further comprises multiple trans-axial x-ray sources.

10. The method of claim 1, wherein the x-ray sources comprise an x-ray tube, a solid state x-ray source, a thermionic x-ray source, a field emitter, a dual anode or combinations thereof.

11. The method of claim 1, wherein the CT axial projection datasets are acquired using a system having a line source in a longitudinal direction, comprising one or more longitudinally offset x-ray source spots.

12. A method for analytically reconstructing a multi-axial computed tomography (CT) dataset, the method comprising:
sequentially acquiring two or more separate CT axial projection datasets using one or more X-ray sources, wherein each CT axial projection dataset comprises a half scan of axial data; and
reconstructing the two or more CT separately acquired axial projection datasets to generate a reconstructed image volume using respective weights determined for one or more voxels of the imaging volume, wherein each respective weight is determined based on at least two factors, wherein the first factor comprises a cone angle for the respective voxel determined primarily along the z-axis and wherein the second factor comprises a degree of redundancy attributable to a voxel being separately illuminated in two or more of the separately acquired CT axial projection datasets.

13. The method of claim 12, wherein the weight for the one or more voxels is determined based upon identifying at least one x-ray source contributing to an illumination of the one or more voxels being back projected.

14. The method of claim 12, wherein the weight for the one or more voxels is determined based upon identifying a cone-angle associated with the one or more x-ray sources that contribute to the illumination of the one or more voxels.

15. The method of claim 12, further comprising determining a weight for one or more voxels that lie in a feathering region, between one or more x-ray source transition points.

16. The method of claim 15, wherein the feathering region comprises at least one of a fixed feathering region width or a variable feathering region width having a fixed transition rate.

17. The method of claim 12, wherein determining the weight for the one or more voxels comprises applying a binary weight for one or more voxels illuminated by a single x-ray source and applying a non-binary weight for one or more voxels that are illuminated by a plurality of x-ray sources, based on the cone-angle associated with the x-ray sources.

18. The method of claim 12, wherein determining the weight for the one or more voxels further comprises determining one or more extrapolated weights for one or more of the voxels that are not illuminated by an x-ray source.

19. The method of claim 12 wherein the x-ray sources comprise an x-ray tube, a solid state x-ray source, a thermionic x-ray source, a field emitter, a dual anode or combinations thereof.

20. The method of claim 12, wherein the one or more x-ray sources are distributed at least longitudinally and further comprise multiple trans-axial x-ray sources.

21. The method of claim 12, wherein the projection datasets are acquired using an Inverse Geometry Computed Tomography (IGCT) system.

22. The method of claim 12, wherein the CT axial projection datasets are acquired using a system having a line source in a longitudinal direction, comprising one or more longitudinally offset x-ray source spots.

* * * * *